United States Patent [19]

Ruben

[11] E Re. 28,486

[45] Reissued July 22, 1975

[54] APPARATUS FOR ARTIFICIAL RESPIRATION OR NARCOSIS

[75] Inventor: Henning M. Ruben, Copenhagen, Denmark

[73] Assignee: Ruth L. Flesse, Testa-Laboratorium A/S, Copenhagen, Denmark

[22] Filed: Nov. 28, 1973

[21] Appl. No.: 419,889

Related U.S. Patent Documents

Reissue of:

[64] Patent No.: 3,650,268
Issued: Mar. 21, 1972
Appl. No.: 839,592
Filed: July 7, 1969

[30] Foreign Application Priority Data

July 8, 1968 Sweden ..... 9387/68

[52] U.S. Cl. ..... 128/145.7; 128/203; 417/471
[51] Int. Cl. ..... A61m 16/00
[58] Field of Search..... 128/145.7, 145.6, 145.5, 128/145.8, 146.4, 158, 203, 204, 205, 188, 231, 232, 247; 417/471, 472, 478

[56] References Cited

UNITED STATES PATENTS

| | | | |
|---|---|---|---|
| 287,681 | 10/1883 | Jensen | 128/232 |
| 1,337,225 | 4/1920 | Heald | 128/145.7 |
| 3,046,978 | 7/1962 | Lea | 128/145.7 |
| 3,262,446 | 7/1966 | Stoner | 128/145.7 |
| 3,291,121 | 12/1966 | Vizneau | 128/145.7 |
| 3,295,523 | 1/1967 | Weichselbaum | 128/232 |
| 3,473,529 | 10/1969 | Wallace | 128/145.7 |

FOREIGN PATENTS OR APPLICATIONS

| | | | |
|---|---|---|---|
| 591,654 | 4/1959 | Italy | 128/145.8 |

*Primary Examiner*—Dalton L. Truluck
*Assistant Examiner*—Henry J. Recla
*Attorney, Agent, or Firm*—Dorfman, Herrell and Skillman

[57] ABSTRACT

An insufflation apparatus for performing artificial respiration or narcosis of the type including a pumping means for moving gas from a gas source to a patient, inlet means for connecting the pumping means to the gas source, outlet means for connecting the pumping means to the air ducts of the patient, and check valve means in each of the inlet means and outlet means for preventing back flow of gas is improved by forming one wall of the pumping means with a resilient membrane. The resilient membrane serves as an elastic means for resisting increases in gas pressures up to a predetermined pressure which will not harm the patient so that gas will be pumped from the pumping means to the patient below that pressure. However, once that predetermined pressure is reached the resilient membrane expands and serves as elastic means compensating forces tending to further increase the gas pressure thereby limiting the over-pressure in this system to said predetermined pressure.

19 Claims, 5 Drawing Figures

INVENTOR.
HENNING MORITZ RUBEN

BY Spencer & Kaye
ATTORNEYS.

INVENTOR.
HENNING MORITZ RUBEN

BY Spencer & Kaye
ATTORNEYS.

APPARATUS FOR ARTIFICIAL RESPIRATION OR NARCOSIS

Matter enclosed in heavy brackets [ ] appears in the original patent but forms no part of this reissue specification; matter printed in italics indicates the additions made by reissue.

BACKGROUND OF THE INVENTION

This invention relates to insufflation apparatus for performing artificial respiration or narcosis, and more particularly to such an apparatus having a resilient membrane serving to prevent pressures in the system from arising beyond a predetermined value which might cause injury to the patient.

Conventional insufflation apparatus generally include a manually compressible pumping means which is self-expanding — at least during operation — i.e., it automatically restores its shape after compression. For such apparatuses the pumping means is provided with at least one first check valve, or inlet valve, for introducing air and/or some other gas into the pumping means. Furthermore, there is provided a second check valve, or outlet valve, at the outlet of the pumping means or at the inlet of a breathing mask or a similar device to which the pumping means is connected either directly or via a suitable gas conduit, said second check valve preventing gas from flowing back from the patient. An apparatus of this type operates in substantially the following manner:

Upon compression of the pumping means the gas contained therein is forced through the outlet valve and therefrom into the air ducts of the patient via the breathing mask. The pumping means is then released and it regains its original shape due to its shape-restoring power during operation conditions. As the pumping means expands it is filled with gas through the inlet valve or valves which are connected to the ambient air and/or to a source of a treating gas such as oxygen or an anesthetic gas.

The pumping means is usually designed as a bag or bladder. The bladders now available are of two different types; one comprising a single wall bladder of a matereial which is at the same time gas-impermeable and shape-restoring, and the other type comprising a double wall bladder which is provided with a self-expanding or shape-restoring insert of, for example, foam rubber and a gas-impermeable outer skin. The double wall bladder has the advantage that it gives a less degree of fatigue during extended use, thereby making it possible for a life-saver to give artificial respiration continuously during a long period of time.

It is a common drawback of both types of the known apparatuses that the indication of dangerous overpressures in the bladder (for example caused by an obstacle in the patient's air ducts) is pereformed on such a subjective basis as the ability of the life-saver to discover pressure changes in the system by means of the feeling in his fingers. This basis for said indication is especially unsuitable when an unpracticed person has to make use of the apparatus.

Since the appearance of too great overpressures in the patient's air ducts can severely damage the patient it has to be ensured that such overpressures cannot appear due to incorrect handling of the apparatus. It has been proposed to solve this problem by providing the bladder with a special pressure relief valve, but there is always a risk for such a valve to be blocked off, whereby the patient can still be subjected to dangerous overpressures, which is especialy dangerous when the bladder is supplied with an anesthetic gas. Another drawback is that the known pressure relief valves must be adjusted to a maximum overpressure which does not harm the patient when appearing during a long period of time. It is, however, important — especially when treating new-born babies — to be able to obtain a higher initial pressure since the first expansion of the lungs requires a considerably higher overpressure (for example 20–40 cm. $H_2O$) than is required for the continued artificial respiration (for example 3–15 cm. $H_2O$).

The present invention provides an apparatus for artificial respiration which completely eliminates the risks for dangerous overpressures to appear in the patient's, air ducts, which is of an extremely simple construction and which, furthermore, allows initial overpressures of short duration which can be dangerous when appearing during a long period of time.

The present invention attacks the problem of pressure limitation from a quite different point of view than do the known constructions. Instead of using separate pressure relief valves the invention provides a pumping means which serves in itself as pressure limitation means, thereby eliminating all movable members which can be blocked off.

According to the invention there is provided an insufflation apparatus for use in a system for artificial respiration or narcosis, said apparatus comprising pumping means having an inlet adapted to be connected to a gas source and an outlet adapted to be brought into communication with the air ducts of a patient via a check valve and check valve means provided in the said inlet and preventing gas from flowing back into the gas source, said apparatus being characterized by at least one thin and gas-tight resilient membrane forming at least a part of the wall of the pumping means and being so elastic that the overpressure in the system cannot exceed a predetermined value, this wall forming membrane thus serving as pressure limitation means. Otherwise stated said membrane should present such elasticity properties that its expansion capacity at small overpressures is not sufficient to annul pressure increases, whereas its expansion capacity at said predetermined overpressure is sufficient for immediate compensation of further pressure increases by means of at least a corresponding increase of the volume of the pumping means, thereby limiting the overpressure in the bladder to said value.

According to a preferred embodiment of the invention the elastic material forming the pressure limiting part is given such properties that upon continuous action from pressure increasing forces the pressure in the bladder will first increase up to a value which can be so high that it would be dangerous to the patient when subjected to this pressure during a longer period of time, but which is completely harmless when being only of short duration, the pressure then falling and being stabilized at a lower pressure value. These pressure values are chosen with respect to the intended field of application and are, for example, different for new-born babies and grown-up persons.

The invention can be utilized in connection with all types of pumping means, bladders as well as piston pumps and similar devices. The expression "pumping means" as used in this application is intended to comprise not only the pump chamber and the walls thereof, but also gas conduits connected thereto. Thus, the pressure limiting membrane or membranes may be arranged as a wall portion of a gas conduit leading from the pump chamber to the patient. When utilizing a single wall bladder the bladder can be made thicker and more resistant in those areas which are actuated by the operator during compression, the rest of the bladder being thinner and sufficiently elastic to serve as the pressure limiting membrane. By such an arrangement it will be possible to construct a bladder which presents very good resistance to repeated compressions while at the same time maintaining the pressure limitation function which is then performed by those parts of the bladder which are normally not effected by the operator.

When the invention is applied to a double wall bladder which is provided with an insert having good self-expansion properties and a gas tight outer skin arranged around the insert, the insert must be provided with channels, passages or other connections for transferring the pressure prevailing in the inner cavity of the bladder to the outer skin which should be so elastic that it can serve as pressure limitation means. Although it is possible to make the insert of a porous material and let the pores in the material serve as the passages transferring the pressure prevailing in the cavity limited by the insert to the outer skin, it is advantageous to provide the insert with special through-channels. The use of a porous material is especially unfavorable when the bladder is supplied with an anesthetic gas, since said gas would be absorbed in a porous material and the patient would be supplied with anesthetic gas even after the supply thereof to the bladder has been cut off.

The elasticity of the membrane or membranes serving as pressure limitation means is such that the overpressure in the system cannot exceed a value of up to about 100 cm. $H_2O$, preferably up to about 60 cm. $H_2O$. According to still another feature of the invention referring to a double wall bladder the channels provided in the insert are adjusted to permit an instantaneous transfer of the pressure prevailing in the inner cavity of the bladder to the outer cavity formed between the insert and the outer skin. Due to this adjustment of the channels it is of importance that no channels be blocked off upon compression of the bladder. It is therefore an important characteristic of the invention that the channels are disposed in such parts of the insert which will not be blocked off upon compression of the bladder. According to a particular embodiment of the invention the channels are disposed near the vertici of an insert shaped as an ellipsoid.

It is also to be noted that the pressure limitation obtained by the present invention not only functions upon activation of the pumping means, but also when the pressure tends to increase due to excess supply of oxygen or anesthetic gas to the system.

These and other advantages and characteristics of the invention will appear from the following detailed description of certain embodiments of an insufflation apparatus according to the invention. In connection with this description reference is made to the enclosed drawings.

IN THE DRAWINGS

Figure 1:
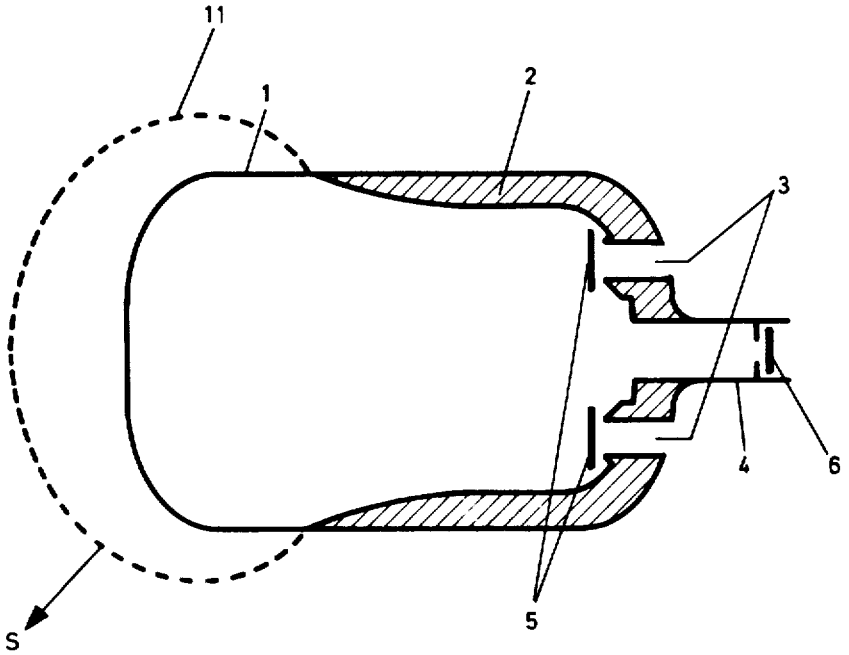
FIG. 1 is a view in axial section illustrating a pumping means according to the invention designed as a single wall bladder.

The bladder shown in FIG. 1 is provided with a first thickwalled part 2 having good self-expansion properties, and a second part 1 which is thinner and sufficiently elastic to serve as pressure limitation means. The bladder is gas tight and provided with one or more channels or connections 3 for supplying gas to the bladder and a connection 4 which is connected to the respiration mask or a similar device to be applied to the patient. Connections 3 are provided with check valves 5 allowing gas to flow only into the bladder. Connection 4 is provided with a check valve 6 allowing gas to flow only in the opposite direction, i.e. from the bladder. The bladder shown in FIG. 1 is provided with two channels or connections 3 which are disposed on both sides of the central connection 4, but it is, of course, possible to make use of a different number of connections disposed in any other possible way without departing from the scope of the invention.

When utilizing the bladder the self-expanding part 2 is compressed. This compression causes an overpressure to appear in the bladder. As a consequence thereof check valves 5 are closed and check valve 6 is opened. The elastic part 1 of the bladder expands and tends to compensate the decrease in volume of the bladder (and accompanying pressure increase) caused by the compression, but the elasticity of the elastic part 1 is not sufficient, at small overpressures, to counterbalance said overpressures. As a consequence thereof the compression of the bladder produces a rapid pressure increase therein up to such pressure values (for example overpressures of 30–60 cm. $H_2O$) which are required for producing inhalation during normal conditions.

At greater overpressurs in the bladder, for example caused by obstacles in the patient's air ducts or excess supply of oxygen or anesthetic gas to the bladder, the elastic part 1 of the bladder becomes more elastic and when the overpressure in the bladder has reached a predetermined value which normally does not harm the patient said part 1 becomes so elastic that any force tending to further increase the pressure in the bladder will immediately be compensated by at least a corresponding expansion of the elastic part 1. In this manner the overpressure in the bladder will not be able to exceed said value. The broken line 11 in FIG. 1 gives an idea of a possible shape of the elastic part 1 after said limit pressure has been reached in the bladder. The arrow S indicates how said part can be further expanded — without pressure increase — when, for example, a further amount of anesthetic gas is supplied into the bladder.

Figure 2:
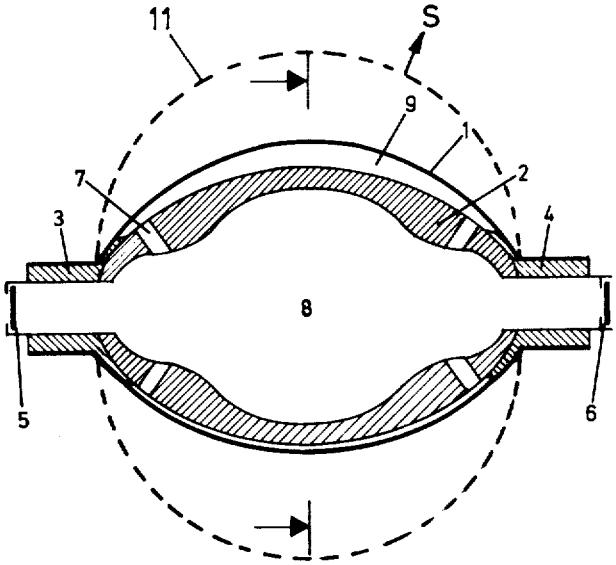
FIG. 2 is a view in axial section of a suitable embodiment of a double wall bladder constructed in accordance with the invention.
Figure 3:
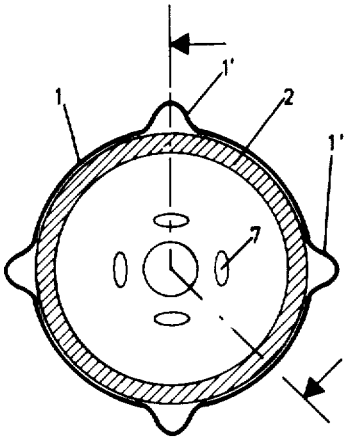
FIG. 3 shows the bladder according to FIG. 2 in cross section.

FIGS. 2 and 3 illustrates how the invention can be applied to a double wall bladder comprising an outer skin 1 which is disposed around a self-expanding insert 2. In this case the outer skin 1, which is made of a gas tight elastic material such as rubber, serves as pressure limitation means. The outer skin can be provided with folds 1', the number of which is four in the embodiment shown in FIGS. 2 and 3. The bladder is further provided with an inlet connection 3 and an outlet connection 4, the outer skin being tightly secured to these connections. The connections 3 is provided with a check valve 5 allowing gas to flow only into the bladder, and connection 4 is provided with a check valve 6 allowing gas to flow only out from the bladder. This connection 4 is either directly or by means of a gas conduit connected to a suitable respiration mask (not shown).

Figure 4:
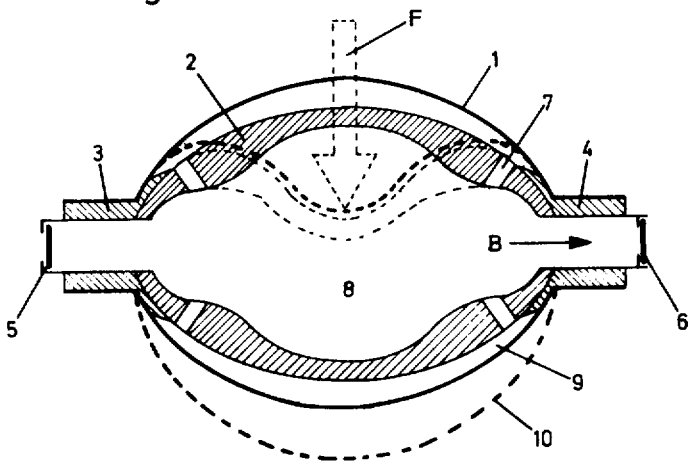
FIG. 4 is a view in axial section illustrating the operation of the bladder according to FIGS. 2 and 3 upon compression of the bladder.

In order to achieve the pressure limitation aimed at the insert 2 is provided with channels 7 interconnecting the inner cavity 8 of the bladder and the outer cavity 9 formed between the insert and the outer skin. In this particular embodiment the insert has approximately the shape of an ellipsoid, the channels 7 being disposed near the vertici of the insert. The apparatus provided with a double wall bladder according to the invention operates in the following manner which is illustrated in FIG. 4:

When the apparatus is to be used connection 4 is connected to a respiration mask which is pressed against the mouth and the nose of the patient. The artificial respiration begins with compression of the bladder (illustrated by the arrow F), thereby forcing the gas contained in the inner cavity 8 into the patient through check valve 6, connection 4 and the respiration mask. When a sufficient volume of gas has been forced into the patient's lungs the operator releases the bladder which regains its original shape due to the shape restoring power of the insert 2, and new gas is sucked into the bladder through inlet valve 5.

Upon compression of the bladder the gas contained in the inner cavity 8 flows not only through check valve 6, but also through the channels 7. In this manner the pressure prevailing in the inner cavity is transferred to the outer cavity 9 formed between the insert 2 and the outer skin 1 by means of the channels 7.

It is not necessary that the outer skin 1 be loosely arranged around the insert in all areas, but it will be sufficient with a loose arrangement of the outer skin only in some portions, the remaining portions of the outer skin being secured, for example bonded, to the insert. In this case the bonded portions of the outer skin are preferably disposed in such parts of the bladder as are compressed by the operator during normal use.

The folds 1' of the outer skin 1 can be used for the indication of relatively small overpressures appearing in the system, the indication being performed by the straightening out of said folds. It is, however, not sufficient to provide indicator means in the form of folds such as 1' since the highest overpressure which can be indicated usually is too low and since an indication of this type requires a continuous surveyance of the shape of the outer skin 1.

The mode of operation of a double wall bladder according to the invention appears from FIGS. 2 and 3. The outer skin of the bladder shown in FIG. 3 has normally the shape indicated in continuous lines. Upon compression of the bladder according to the arrow F the gas contained in the inner cavity 8 is forced into the patient (arrow B), on the one hand, and in to the outer cavity 9, on the other hand. It is assumed in FIG. 4 that the patient's air ducts are completely or partly obstructed such that the gas flow according to the arrow B decreases or terminates, whereby dangerous overpressures can appear in the system. According to the invention such a dangerous situation cannot appear since the outer skin is so elastic that any tendency to dangerous overpressure in the system will immediately be compensated by at least a corresponding expansion of the outer skin as indicated by the broken line 10 in FIG. 3.

The operation of the bladder according to FIGS. 2, 3 and 4 will consequently be such that compression of the bladder during normal conditions of operation (no obstacles in the patient's air ducts, no excessive supply of anesthetic gas to the bladder) produces an overpressure in the bladder which is sufficient to overcome the resistance in the patient's air ducts and produce artificial inhalation, whereas compression of the bladder when the pressure therein has reached a predetermined limit value (which normally is not dangerous to the patient) produces an increase of the volume of the bladder (by expansion of the outer skin 1) which is at least as great as the decrease in volume caused by the compression.

FIG. 2 illustrates the case when an overpressure is built-up in the system due to continuous supply of, for example, anesthetic gas and not by compression of the bladder. Also in this Figure the normal shape of the outer skin 1 is indicated in continuous lines, the shape of the outer skin after the highest permitted overpressure has been built-up in the system being illustrated by the broken line 11. Any additional supply of gas to the bladder which tends to increase the pressure therein will be compensated by a further expansion of the outer skin in the direction of the arrow S.

Figure 5:
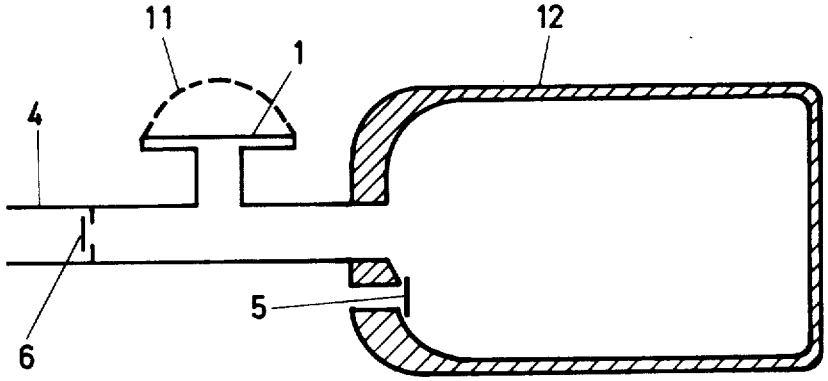
FIG. 5 is a view in axial section illustrating a pressure-limitation means according to the invention which can be applied to any type of pump suitable for producing insufflation in an apparatus for artificial respiration or narcosis.

According to the embodiment illustrated in FIG. 5 the resilient-membrane 1 serving as pressure limitation means is disposed in an outlet conduit from the pump chamber 12 instead of forming a part of the wall of said chamber. More precisely the membrane 1 forms an end closure of a short branch connected to said outlet conduit of the pumping means. The operation of the membrane is also in this case the same as according to the embodiments shown in FIGS. 1–4, the expansion of the membrane 1 in response to forces tending to increase the pressure in the system being indicated by the broken line 11. The pumping means shown in FIG. 5 is a gas-tight single wall bladder 12, but this embodiment is preferably used together with another type of pump, for example a piston pump, the walls of which cannot easily be provided with a pressure limiting membrane.

The invention is not intended to be limited to the examples of embodiments given in the foregoing and it is readily apparent that a large number of alternative forms remain possible within the scope of the invention. Thus, the pumping means, especially the bladder can be given some other shape than shown in the drawings, the connection for introducing gas into the bladder and discharging gas therefrom can be disposed in any other suitable way, and the channels interconnecting the inner and outer cavities of the double wall bladder can be disposed in other parts of the bladder and the number of channels can be more or fewer than shown in the drawings. The number, size and disposition of the pressure limiting membrane or membranes can be altered in many different ways while maintaining the pressure limitation effect obtained by the invention. It is, for example, possible to construct a single wall bladder having circumferential portions which are alternatingly thick and thin, the thick portions being self-expanding and the thin portions serving as pressure limitation means.

I claim:

1. In insufflation apparatus for performing artificial respiration in narcosis, which apparatus includes pumping means for moving gas from a gas source to a patient, the pumping means having a gas containing portion defined by enclosing walls, inlet means on said pumping means for connecting the latter to a gas source and including check valve means for preventing back flow of the gas from the pumping means to the gas source, and outlet means on said pumping means connecting the pumping means to the air ducts of a patient including check valve means for preventing gas from flowing from the air ducts of the patient into the pumping means, said outlet means including an outlet conduit, the improvement which comprises: a first wall section and a second wall section forming the walls of the gas containing portion of the pumping means, said first wall section consisting of a membrane that is more resilient than said second wall section, said membrane forming a portion of the wall of said outlet conduit and being disposed between said check valve means of said outlet means and said second wall section, said membrane being movable between an unexpanded position when the gas pressure in the pumping means is below a predetermined pressure and, under the influence of the gas when the pressure thereof exceeds said predetermined pressure, an expanded position, said membrane thus constituting a means for increasing the volume of the gas containing portion of the pumping means, in consequence of which the pressure of the gas in the pumping means is limited to said predetermined pressure.

2. The improvement defined in claim 1, wherein said membrane forms an end closure of a short branch of said outlet conduit.

3. The improvement defined in claim 1, wherein said first and second wall sections are integrally connected to each other.

4. In insufflation apparatus for performing artificial respiration in narcosis, which apparatus includes pumping means for moving gas from a gas source to a patient, the pumping means having a gas containing portion defined by enclosing walls, inlet means on said pumping means for connecting the latter to a gas source and including check valve means for preventing back flow of the gas from the pumping means to the gas source, and outlet means on said pumping means connecting the pumping means to the air ducts of a patient including check valve means for preventing gas from flowing from the air ducts of the patient into the pumping means, the improvement which comprises: a first wall section and a second wall section forming the walls of the gas containing portion of the pumping means, said first wall section consisting of a membrane that is more resilient than said second wall section and that is movable between an unexpanded position when the gas pressure in the pumping means is below a predetermined pressure and, under the influence of the gas when the pressure thereof exceeds said predetermined pressure, and expanded position, said membrane thus constituting means for increasing the volume of the gas containing portion of the pumping means, in consequence of which the pressure of the gas in the pumping means is limited to said predetermined pressure; said pumping means including a bladder which is gas-impermeable, said bladder being connected between said inlet and outlet means, said bladder being compressible under applied force to expel gas through said outlet means and being self-expanding from a compressed position to draw gas into said pumping means through said inlet means during a cycle of operation, said bladder having a double wall including an inner wall formed by said second wall section and which is compressible and self-expanding from a compressed position, said membrane forming an outer wall which is gas-impermeable and encompasses said inner wall, said inner wall and said outer wall being connected to each other only at spaced apart positions between said outlet means and said inlet means, and there being channels for gas extending through said inner wall.

5. The improvement as defined in claim 4, wherein said outer wall has a plurality of folds therein.

6. The improvement as defined in claim 4, wherein said inner wall has a shape of an ellipsoid and said channels are disposed near the vertici of said inner wall.

7. The improvement as defined in claim 4, wherein said channels are located between the spaced apart positions and provide for a gas flow through said inner wall when the gas is at a pressure above said predetermined pressure.

8. The improvement as defined in claim 4, wherein said channels are a means for providing a total flow capacity which is sufficient to immediately urge said outer wall to an expanded position when the gas is at a pressure above said predetermined pressure.

9. *In insufflation apparatus for performing artificial respiration or narcosis, which apparatus includes pumping means for moving gas from a gas source to a patient, the pumping means having a gas containing portion defined by enclosing walls, inlet means on said pumping means for connecting the latter to a gas source and including check valve means for preventing back flow of the gas from the pumping means to the gas source, and outlet means on said pumping means connecting the pumping means to the air ducts of a patient including check valve means for preventing gas from flowing from the air ducts of the patient into the pumping means, the improvement which comprises: a first wall section and a second wall section forming the walls of the gas containing portion of the pumping means, said first wall section being an elastic member that is more expandable than the second wall section and that is movable between an unexpanded position when the gas pressure in the pumping means is below a predetermined pressure and, under the influence of the gas when the pressure thereof exceeds said predetermined pressure, and expanded position; said elastic member thus constituting means for increasing the volume of the gas containing portion of the pumping means, in consequence of which the pressure of the gas in the pumping means is limited to said predetermined pressure; said pumping means including a bladder connected between said inlet and outlet means, said bladder being compressible under applied force to expel gas through said outlet means and being self-expanding from*

*a compressed position to draw gas into said pumping means through said inlet means, said bladder having a double wall including an inner wall formed by said second wall section and which is compressible and self-expanding from a compressed position, said elastic member forming an outer wall which is gas-impermeable and encompasses said inner wall, said inner wall having channels for gas extending through said inner wall.*

*10. Insufflation apparatus for performing artificial respiration or narcosis, comprising: pumping means, inlet means on said pumping means for connecting the pumping means to a gas source and having valve means for preventing gas flow from the pumping means to the gas source, outlet means on said pumping means for directing gas from the pumping means to a patient and having valve means for preventing gas flow from the patient into the pumping means, said pumping means including a bladder connected between said inlet means and said outlet means and being compressible under applied force to expel gas and self-expanding from a compressed condition to cause gas to be drawn into said bladder, said bladder having a double wall including an inner wall and an outer wall, said inner wall being self-expanding after being compressed and having channels through the wall to permit gas to flow through the inner wall, said outer wall being disposed around the inner wall and being gas-impermeable, said outer wall being formed of an elastic material which is more expandable than the inner wall and which is movable between an unexpanded condition when the gas pressure in the pumping means is below a predetermined pressure and an expanded condition when the gas pressure exceeds said predetermined pressure, whereby said outer wall provides means for increasing the volume of the pumping means when said predetermined pressure is exceeded.*

*11. The insufflation apparatus of claim 10 in which said outer wall is provided with a plurality of folds.*

*12. The insufflation apparatus of claim 10 in which said inner wall has a shape of an ellipsoid and said channels are disposed near the vertici of said inner wall.*

*13. The insufflation apparatus of claim 10 in which said channels are a means for providing a total flow capacity which is sufficient to immediately urge said outer wall to an expanded condition when the gas is at a pressure above said predetermined pressure.*

*14. The insufflation apparatus of claim 10 in which the channels are disposed to be located in the inner wall in positions to be free from the outer wall upon desired compression of the bladder so that the outer wall limits the gas pressure in the pumping means to said predetermined pressure.*

*15. The insufflation apparatus of claim 10 in which said channels are a means for providing a gas flow capacity which is sufficient to prevent pressure in excess of said predetermined pressure from occurring in the bladder when a high frequency of compression occurs.*

*16. The insufflation apparatus of claim 10 in which said channels are a means for providing a gas flow capacity which is sufficient to prevent pressure of gas in excess of said predetermined pressure from occurring in the bladder when an excess amount of gas is introduced through said inlet means into the bladder.*

*17. Insufflation apparatus for performing artificial respiration or narcosis, comprising pumping means, inlet means for connecting the pumping means to a gas source and having valve means for preventing gas flow from the pumping means to the gas source, outlet means for directing gas from the pumping means to a patient and having valve means for preventing gas flow from the patient and having valve means for preventing gas flow from the patient into the pumping means, said pumping means having a gas containing portion defined by enclosing walls and connecting said inlet means to said outlet means, said pumping means including a first wall part and a second wall part integrally connected to the first wall part to form a single wall member providing the gas containing portion, said first wall part being compressible under applied force to expel gas and self-expanding from a compressed condition to cause gas to be drawn into said pumping means, said second wall part being formed of an elastic material which is more expandable than the first wall part and is movable between an unexpanded condition when the gas pressure in the pumping means is below a predetermined pressure and an expanded condition when the gas pressure exceeds said predetermined pressure, whereby said second wall part increases the volume of the gas containing portion of the pumping means when said predetermined pressure is exceeded.*

*18. The insufflation apparatus of claim 17 in which the second wall part forms an end wall of the gas containing portion to be free to expand when the gas pressure exceeds said predetermined pressure.*

*19. The insufflation apparatus of claim 18 in which the second wall part is thinner than the second wall part to permit the volumetric expansion upon the occurrence of pressure tending to increase the gas pressure in the pumping means beyond the predetermined pressure.*

* * * * *

UNITED STATES PATENT OFFICE

CERTIFICATE OF CORRECTION

Patent No. RE28,486 Dated July 22, 1975

Inventor(s) Henning M. Ruben

It is certified that error appears in the above-identified patent and that said Letters Patent are hereby corrected as shown below:

Column 1, line 47, "matereial" should be --material--;

Column 1, line 58, "pereformed" should be --performed--;

Column 4, line 52, "overpressurs" should be --overpressures--;

Column 5, line 3, "illustrates" should be --illustrate--;

Column 5, line 13, "connections" should be --connection--;

Column 7, line 12, after "respiration" delete "in" and insert --or--;

Column 7, line 49, after "respiration" delete "in" and insert --or--; and

Column 8, line 2, before "expanded" delete "and" and insert --an--.

Signed and Sealed this

*twenty-first* Day of *October 1975*

[SEAL]

*Attest:*

RUTH C. MASON
*Attesting Officer*

C. MARSHALL DANN
*Commissioner of Patents and Trademarks*